US012026456B2

(12) United States Patent
Weeks

(10) Patent No.: US 12,026,456 B2
(45) Date of Patent: Jul. 2, 2024

(54) SYSTEMS AND METHODS FOR USING OPTICAL CHARACTER RECOGNITION WITH VOICE RECOGNITION COMMANDS

(71) Applicant: Dolbey & Company, Inc., Cincinnati, OH (US)

(72) Inventor: Curtis A. Weeks, Loveland, OH (US)

(73) Assignee: DOLBEY & COMPANY, INC., Cincinnati, OH (US)

( * ) Notice: Subject to any disclaimer, the term of this patent is extended or adjusted under 35 U.S.C. 154(b) by 415 days.

(21) Appl. No.: 15/670,047

(22) Filed: Aug. 7, 2017

(65) Prior Publication Data

US 2019/0042186 A1    Feb. 7, 2019

(51) Int. Cl.
| | |
|---|---|
| *G06F 40/174* | (2020.01) |
| *G06F 3/0481* | (2022.01) |
| *G06F 3/04842* | (2022.01) |
| *G06F 3/04845* | (2022.01) |
| *G06F 3/16* | (2006.01) |
| *G06F 40/103* | (2020.01) |
| *G06F 40/232* | (2020.01) |

(Continued)

(52) U.S. Cl.
CPC .......... *G06F 40/174* (2020.01); *G06F 3/0481* (2013.01); *G06F 3/04845* (2013.01); *G06F 3/167* (2013.01); *G06F 40/232* (2020.01); *G06V 10/56* (2022.01); *G06V 30/153* (2022.01); *G06V 30/412* (2022.01); *G06V 30/414* (2022.01); *G10L 15/22* (2013.01); *G16H 10/60* (2018.01); *G16H 40/63* (2018.01); *G06F 3/04842* (2013.01); *G06F 40/103* (2020.01); *G10L 2015/223* (2013.01)

(58) Field of Classification Search
CPC .... G06F 3/167; G06F 3/0481; G06F 3/04845; G06F 17/243; G06F 40/232; G06F 40/174; G06F 40/103; G06F 3/04842; G16H 10/60; G16H 10/63; G16H 40/63; G06K 9/00449; G06K 9/00463; G06K 9/344; G06K 9/4652; G10L 15/22; G10L 2015/223; G06V 10/56; G06V 30/153; G06V 30/412; G06V 30/414
See application file for complete search history.

(56) References Cited

U.S. PATENT DOCUMENTS 5,764,799 A    6/1998  Hong et al.
5,875,428 A *  2/1999  Kurzweil ............. G09B 17/003
                                                    704/260
(Continued)

OTHER PUBLICATIONS

Azzola, Francesco; Using Your Voice and Android to Control IoT devices (Year: 2017).*

*Primary Examiner* — Stephen S Hong
*Assistant Examiner* — Carl E Barnes, Jr.
(74) *Attorney, Agent, or Firm* — Dinsmore & Shohl LLP

(57) ABSTRACT

Systems and methods for using optical character recognition (OCR) with voice recognition commands are provided. Some embodiments include receiving a user interface that includes a text field, capturing an image of at least a portion of the user interface, and performing OCR on the image to identify the text field and a word in the user interface. Some embodiments include mapping a coordinate of the word in the text field, receiving a voice command that includes the word, and navigating, by the computing device, a cursor to the coordinate to execute the voice command.

20 Claims, 12 Drawing Sheets

(51) Int. Cl.
*G06V 10/56* (2022.01)
*G06V 30/148* (2022.01)
*G06V 30/412* (2022.01)
*G06V 30/414* (2022.01)
*G10L 15/22* (2006.01)
*G16H 10/60* (2018.01)
*G16H 40/63* (2018.01)

(56) References Cited

U.S. PATENT DOCUMENTS

| | | | |
|---|---|---|---|
| 6,587,822 B2 | 7/2003 | Brown et al. | |
| 6,839,669 B1 * | 1/2005 | Gould | G10L 15/22 |
| | | | 704/246 |
| 7,496,230 B2 | 2/2009 | Chen et al. | |
| 7,706,611 B2 | 4/2010 | King et al. | |
| 7,801,730 B1 * | 9/2010 | Miyazaki | G10L 15/26 |
| | | | 704/275 |
| 8,175,230 B2 * | 5/2012 | Bangalore | H04L 12/6418 |
| | | | 379/88.17 |
| 8,447,066 B2 | 5/2013 | King et al. | |
| 9,147,275 B1 * | 9/2015 | Hyde-Moyer | G06T 11/60 |
| 9,792,708 B1 * | 10/2017 | Hyde-Moyer | G06T 11/60 |
| 2003/0085162 A1 | 5/2003 | Daniels, Jr. et al. | |
| 2003/0158736 A1 * | 8/2003 | James | G06F 3/167 |
| | | | 704/E15.044 |
| 2005/0021343 A1 * | 1/2005 | Spencer | G09B 5/06 |
| | | | 704/275 |
| 2005/0288932 A1 | 12/2005 | Kurzweil et al. | |
| 2008/0137971 A1 | 6/2008 | King et al. | |
| 2008/0141117 A1 * | 6/2008 | King | G06Q 30/02 |
| | | | 715/238 |
| 2008/0270110 A1 | 10/2008 | Yurick et al. | |
| 2010/0177970 A1 | 7/2010 | King et al. | |
| 2011/0035656 A1 * | 2/2011 | King | H04N 1/00331 |
| | | | 715/234 |
| 2011/0123115 A1 * | 5/2011 | Lee | G06K 9/036 |
| | | | 382/185 |
| 2011/0301943 A1 * | 12/2011 | Patch | G10L 15/265 |
| | | | 704/9 |
| 2014/0108010 A1 * | 4/2014 | Maltseff | G06F 3/167 |
| | | | 704/235 |
| 2014/0162751 A1 * | 6/2014 | Ryan | G07F 17/3244 |
| | | | 463/20 |
| 2014/0222805 A1 * | 8/2014 | Huang | G16H 10/60 |
| | | | 707/732 |
| 2015/0199320 A1 * | 7/2015 | Ho | G06F 3/017 |
| | | | 715/233 |
| 2016/0034253 A1 * | 2/2016 | Bang | G06F 3/04883 |
| | | | 715/728 |
| 2018/0225277 A1 * | 8/2018 | Alba | G06F 17/277 |

* cited by examiner

SYSTEMS AND METHODS FOR USING OPTICAL CHARACTER RECOGNITION WITH VOICE RECOGNITION COMMANDS

TECHNICAL FIELD

Embodiments described herein generally relate to systems and methods for using optical character recognition (OCR) with voice recognition commands and, more specifically, to using OCR to facilitate voice control of formatting and navigation commands.

BACKGROUND

Users of voice recognition applications typically use voice commands to control the target applications they are using. Traditionally, this functionality is accomplished using operating system application program interfaces (APIs), target application APIs, and/or target applications text control APIs that the voice application interfaces with to perform certain voice commands actions. This approach may function for target applications that expose the API functionality necessary to support the automation needed for performing the desired commands. However, many target applications do not embed speech recognition functionality, and not all target applications provide APIs to allow for commands Another problem with existing solutions is that a target application may have multiple text fields whereas only one text field is active for editing at a time. For example, an electronic health record (EHR) application may have a text field on the screen for the "chief complaint" and another text field on the screen for the "physical exam." These current solutions may only provide access to the current active text field, and not allow voice commands access to read the text from other text fields in the target application until the user first activates them.

This particular problem is necessarily rooted in computer and network technology, specifically arising in the health care market. For example, many EHR applications now run as virtual applications (for example, using Citrix® XenApp®) in a cloud hosted environment limiting access to traditional APIs.

SUMMARY

Systems and methods for using optical character recognition (OCR) with voice recognition commands are provided. Some embodiments include receiving a user interface that includes a text field, capturing an image of at least a portion of the user interface, and performing OCR on the image to identify the text field and a word in the user interface. Some embodiments include mapping a coordinate of the word in the text field, receiving a voice command that includes the word, and navigating, by the computing device, a cursor to the coordinate to execute the voice command.

In another embodiment, a system includes a computing device that includes a memory component and a processor. The memory component may store application logic, OCR logic, and voice recognition logic that, when executed by the processor, causes the computing device to receive, via the application logic, a user interface that includes a text field. The system may additionally capture, via the voice recognition logic, an image of at least a portion of the user interface, perform, via the OCR logic, recognition on the image to identify the text field and a word in the user interface, and map, via the voice recognition logic, a coordinate of the word in the text field. Some embodiments may cause the system to receive, via the voice recognition logic, a voice command that includes the word, navigate, via the voice recognition logic, a cursor to the coordinate, and execute, via the voice recognition logic, the voice command in the target application.

In yet another embodiment, a non-transitory computer-readable medium for using optical character recognition (OCR) with voice recognition commands is provided. When executed by a computing device the non-transitory computer-readable medium causes the computing device to receive a user interface that includes a text field, capture an image of at least a portion of the user interface, and perform OCR on the image to identify the text field and a word in the text field. The non-transitory computer-readable medium may also cause the computing device to map a coordinate of the word in the text field, receive a voice command that includes the word, navigate a cursor to the coordinate, and execute the voice command in a target application.

These and additional features provided by the embodiments of the present disclosure will be more fully understood in view of the following detailed description, in conjunction with the drawings.

BRIEF DESCRIPTION OF THE DRAWINGS

The embodiments set forth in the drawings are illustrative and exemplary in nature and not intended to limit the disclosure. The following detailed description of the illustrative embodiments can be understood when read in conjunction with the following drawings, where like structure is indicated with like reference numerals and in which:

FIG. 3 depicts a user interface indicating text fields for providing voice text formatting and navigation commands, according to embodiments described herein;

FIG. 6 depicts a user interface that identifies options when a voice command applies to a plurality of sections of a text field, according to embodiments described herein;

DETAILED DESCRIPTION

Embodiments disclosed herein include systems and methods for using optical character recognition with voice recognition commands. Some embodiments provide a voice recognition application using optical recognition techniques on the text with additional techniques. The embodiments improve accuracy and performance specifically for capturing text in identified text fields from a target application for speech recognition purposes.

Some embodiments may be configured to capture a spoken audio command and process that audio together with a speech grammar built from the captured text with a speech recognition engine. Upon recognizing the desired voice command, these embodiments may determine which captured text to utilize and execute the command. Embodiments also determine and utilize a coordinate and automated mouse clicks to automatically select text from screen captured text and use simulated key strokes to select text to perform the desired command. In the event of multiple matches between the voice command and the captured text, some embodiments display indicators on the screen from which the user can use additional voice commands or microphone buttons to navigate and select a particular indicator.

Accordingly, some embodiments are configured to read text fields provided by the target application, then use that recognized text together with known text to dynamically create a speech grammar. When a match is found between the user's voice command and the speech grammar, embodiments may use the identified text coordinates in the user interface to simulate mouse selections for performing the command.

As an example, a target application may provide a text field with the words: "The patient was a 55-year-old female who reports to the ER with chest pain." When the user initiates the voice command, the speech application performs OCR (or other) text recognition; builds a speech grammar out of the recognized text; and processes the audio together with the speech grammar to recognize a voice command. Examples of voice commands applicable to this system:

"SELECT [word or phrase]."
"SELECT [word] THROUGH [word]."
"INSERT BEFORE [word or phrase]."
"INSERT AFTER [word or phrase]."
"CUT [word or phrase]."
"COPY [word or phrase]."
"CUT [word] THROUGH [word]."
"COPY [word] THROUGH [word]."
"PASTE BEFORE [word or phrase]."
"PASTE AFTER [word or phrase]."
"PASTE AFTER [punctuation] AFTER [word or phrase]."
"PASTE BEFORE [punctuation] AFTER [word or phrase]."
"CAPITALIZE [word or phrase]."
"DELETE [word or phrase]."
"LOWERCASE [word or phrase]."
"BOLD [word or phrase]."
"ITALICIZE [word or phrase]."
"UNDERLINE [word or phrase]."

The above voice commands are only examples of the possible commands. Other formatting and navigation commands are also included within the scope of this disclosure. The systems and methods for using optical character recognition with voice recognition commands incorporating the same will be described in more detail, below.

Figure 1:
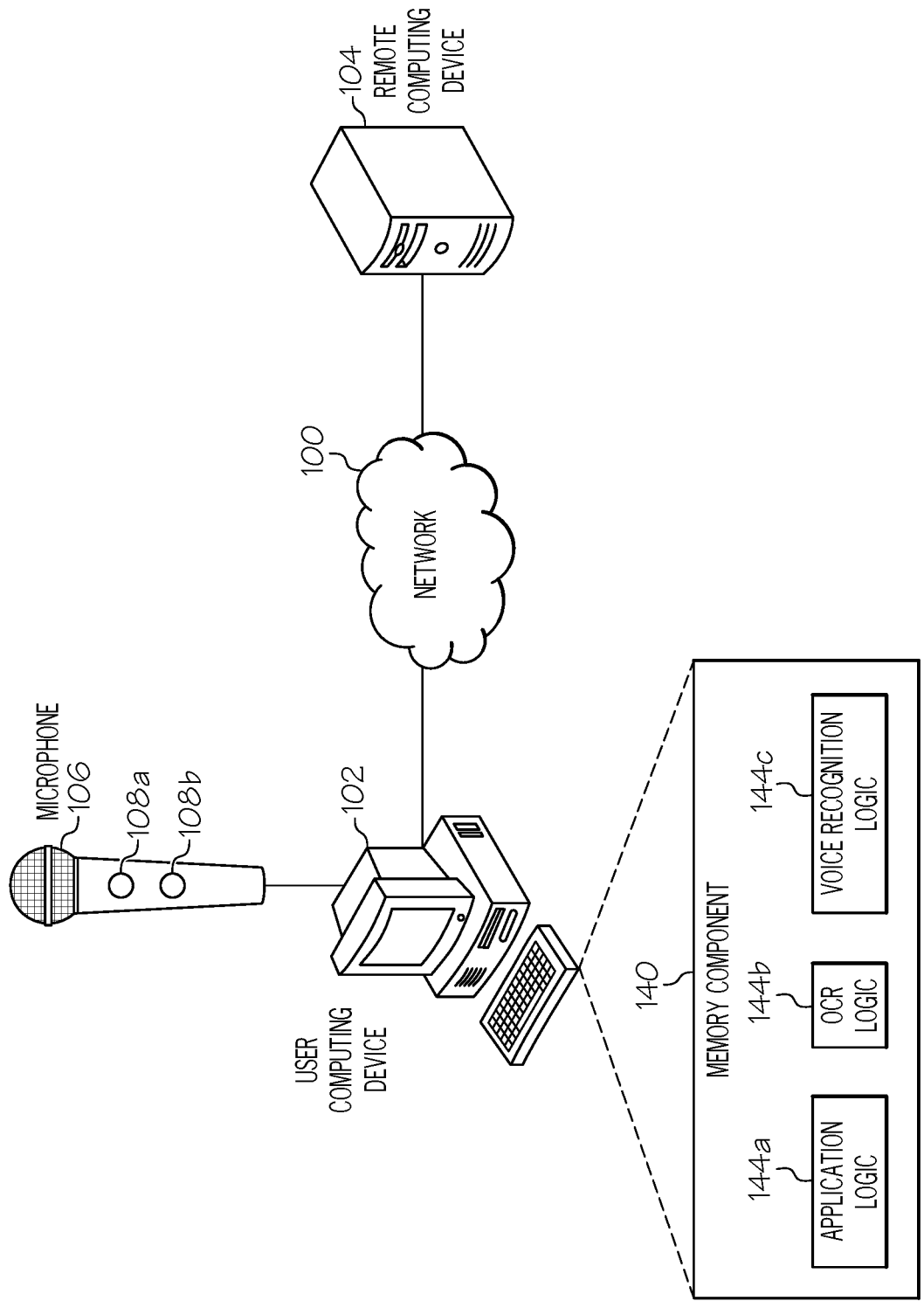
FIG. 1 depicts a computing environment for using optical character recognition with voice recognition commands, according to embodiments described herein.

Referring now to the drawings FIG. 1 depicts a computing environment for using optical character recognition with voice recognition commands, according to embodiments described herein. As illustrated, the computing environment includes a network 100, a user computing device 102, and a remote computing device 104. The network 100 may include any wide area network (such as the internet, a cellular network, a public, etc.), local network (such as a local area network, Wi-Fi network, etc.) and/or any near field network (such as via near field communication, Bluetooth, etc.) for communicating data between the user computing device 102 and the remote computing device 104.

The user computing device 102 may include any personal computer, laptop, tablet, mobile device, and/or other device that includes and/or provides a user interface (such as a monitor, keyboard, mouse, touchscreen, etc.) and otherwise performs the functionality described herein. The user computing device 102 may include and/or be coupled to a microphone 106 for receiving voice commands from a user. In some embodiments, the microphone 106 may include one or more input devices 108*a*, 108*b* for receiving additional user input.

The user computing device 102 may additionally include a memory component 140, which stores application logic 144*a*, OCR logic 144*b*, and voice recognition logic 144*c*. The application logic 144*a* may cause the user computing device 102 to provide an application that includes a word processing component, text input component, etc. The OCR logic 144*b* may be included with the application logic 144*a* and/or may be a standalone piece of logic. Regardless, the OCR logic 144*b* may be configured for analyzing an image that includes unrecognized text and decipher and convert the unrecognized text into editable text. The voice recognition logic 144*c* may cause the user computing device 102 to receive a voice command (such as from the microphone 106) and implement the voice command on the application logic 144*a*. Depending on the embodiment, the voice recognition logic 144*c* may be included as part of the application logic 144*a*, the OCR logic 144*b*, and/or may be a standalone component.

The remote computing device 104 may include similar components as the user computing device 102, but may be configured as a server, personal computer, laptop, tablet, mobile device, etc. Depending on the particular embodiment none, one, ore more than one of the application logic 144*a*, the OCR logic 144*b*, the voice recognition logic 144*c*, and/or functionality described herein may be stored and executed by the remote computing device 104 and provided to the user computing device 102 via the network 100.

Figure 2:
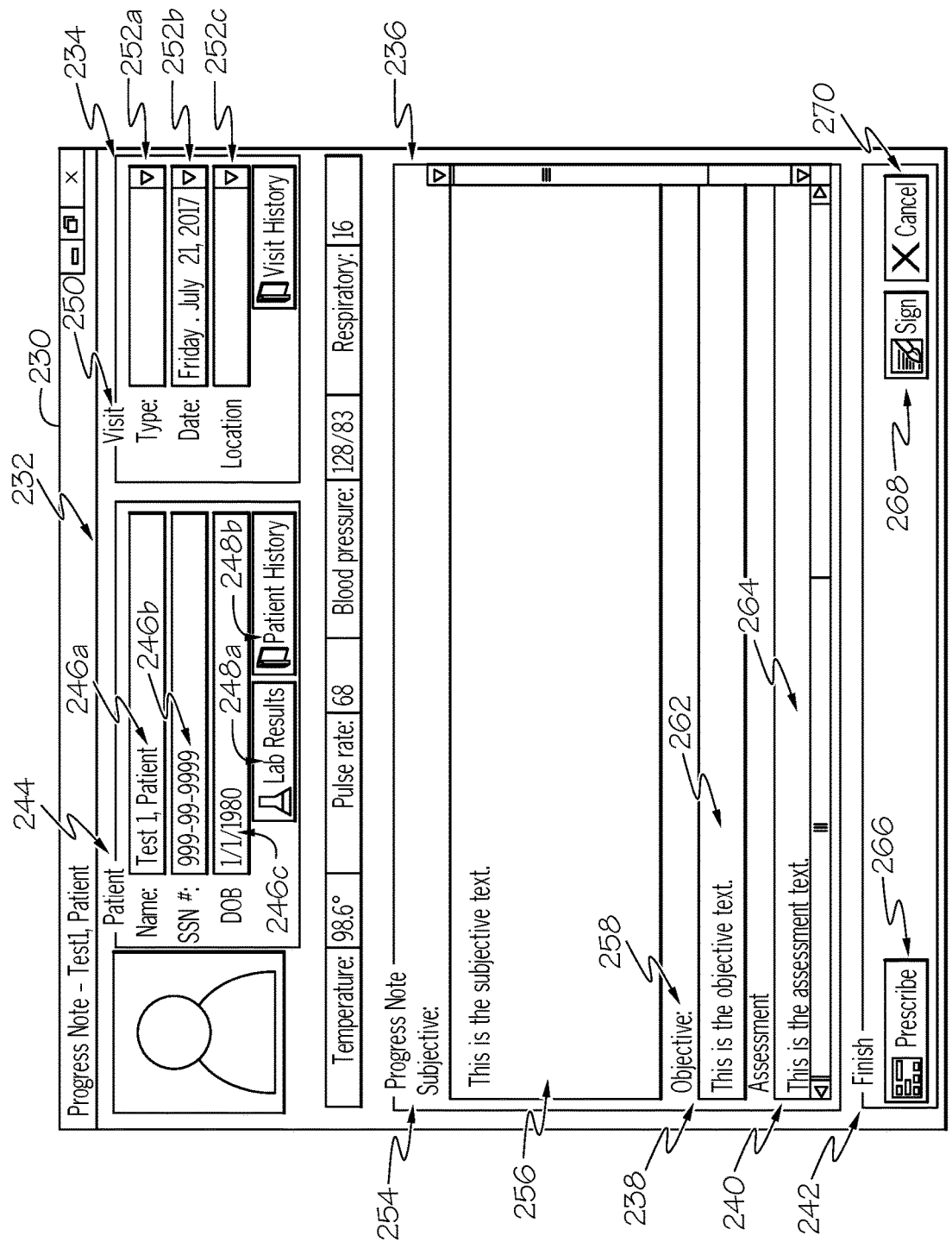
FIG. 2 depicts a user interface for using optical character recognition with voice recognition commands, according to embodiments described herein.

FIG. 2 depicts a user interface 230 for using optical character recognition with voice recognition commands, according to embodiments described herein. As illustrated, the user interface 230 includes a patient section 232, a visit section 234, a note section 236, an objective section 238, as assessment section 240, and a finish section 242. The patient section 232 includes a non-text field 244, and text fields 246*a*, 246*b*, 246*c*. Also provided are user options 248*a*, 248*b*.

The visit section 234 includes a non-text field 250, as well as text fields 252*a*, 252*b*, 252*c*. The note section 236 includes a non-text field 254 and a text field 256. The objective section 238 includes a non-text field 258 and a text field 262. The assessment section 240 includes a non-text field 258 and a text field 264. The finish section 242 includes a prescribe option 266, a sign option 268, and a cancel option 270.

In operation, the user may dictate, type, or otherwise input text into one or more of the text fields. In some embodiments, the input text is already recognized; however some embodiments include unrecognized text. The user may then provide a voice command associated with the text. As described above, the voice command may include a formatting command such as "BOLD patient," which would mean that the user wants the word "patient" bolded. Also, as described above, the voice command may include a navigation command such as "INSERT BEFORE patient," which would mean the user wants to place the text input location before "patient". Accordingly, the text recognition process could be performed at the same time as the user is dictating the voice command, such that words provided in the speech grammar for the voice command recognition step are up to date to what is currently on the user's computer screen. In some embodiments, the time to perform the text recognition process may take longer than it takes for the user to speak the voice command. Thus, the text recognition process may be performed at any time to provide the desired response time for the voice command. Accordingly, some embodiments of the voice recognition logic 144c (FIG. 1) may anticipate with a trigger event when a user may speak a voice command that may require text from the text recognition process.

Accordingly, embodiments may be configured to automatically capture an image (i.e. snapshot) of the user interface 230 into an image. This screen capture may include the entire screen and/or it may be just the active target application or active control within the target application and/or user interface 230. In addition to performing OCR to recognize the text in the captured image, some embodiments identify and/or map the exact coordinates for each identified word (and/or a plurality of words) on the screen such that voice command execution process can be performed successfully.

Embodiments may be configured to scan the image object for likely text fields where a user may want to dictate and use formatting and navigation voice commands. In many target applications (such as depicted in FIG. 2), these areas have a least a one pixel white (or close to white) rectangular border around them. So in order to filter out the non-text fields, embodiments may subdivide the captured image object into subsections for each possible text field. Some white bordered regions of the screen may contain inner white rectangular areas such that only the inner text fields are applicable text fields. Additionally, likely text fields may have a minimum height and width. For example, small white rectangular areas are not likely candidates for formatting and navigation commands.

Accordingly, referring again to FIG. 2, after the image of the user interface 230 is captured, embodiments may detect the text fields 246a, 246b, 246c, 252a, 252b, 252c, 256, 262, and 264. Within this embodiment, the identified text areas in the full captured image may be divided into smaller separate images that are each processed separately through the OCR logic 144b in order to improve performance. These areas may be identified as text fields due to the size, color, border, etc. Additionally, to accommodate a wide range of target applications, the following options may be used to refine the process for the particular target application. These options may be administratively selected and/or provided via one or more user options, depending on the embodiment.

Only process target color text fields: These embodiments may be configured to control whether the entire captured image is processed or whether the image should be separated into text field areas and only those should be processed. Text fields are ones with at least one solid white line (1 pixel or greater) around them and/or include other characteristics indicative of a text field. Embodiments may also be configured to support an alternate color should the target application not use white as the standard background for text fields. Text field rectangles can best be identified by scanning the top, bottom, and right borders only and omitted the left border. This improves overall performance and also supports editors where there is not full target color pixel border between the text on the left side and the text border area.

Maximum threshold RGB value: This option may be utilized with Only Process Target Color Text Fields and/or with Minimum Threshold RGB Value (above) to allow for searching for a particular color range for text fields, since many target applications use white as the text background this may be set to 255.

Minimum threshold RGB value: This option may be used with Only Process Target Color Text Fields (above). Only pixels with an RGB value between the stated value and the maximum will be considered as border colors for text fields. Some text fields may not be a single color around the entire border because the application or operating system may utilize image blending effects. Pure white has an RGB (red, green, and blue) setting of 255, 255, 255. If set to 242, each RGB value must be 242 or higher. If a value less than this value is found then the pixel is not considered to match the target color.

Minimum text field height: This option is used together with Only Process Target Color Text Fields and controls what is considered the minimum height for a valid text field.

Minimum text field width: This option is used together with Only Process Target Color Text Fields and controls what is considered the minimum width of a text field.

Trim text field: This option is used together with Only Process Target Color Text Fields and controls whether the text fields that are found are further trimmed down such that extra empty space is not sent through the OCR engine. The smaller and fewer areas that are processed through the OCR logic 144b, the better the performance.

Minimum text field border: This option may be used together with Trim Text fields. When the text fields are trimmed down embodiments may be configured to control the amount of margin of white space (in pixels) to leave in place around the text fields.

After filtering the image through text area processing, areas that do not meet the specified requirements, such as the non-text field 244 and the non-text field 250 may be excluded. The remaining white text fields may be extracted and further reduced to include only the areas that include text. Additional image manipulation prior to processing by the OCR logic 144b, can further help improve the accuracy and speed. These could include but are not limited to:

Scale factor: This option includes determining an amount to enlarge the image prior to submitting the image to the OCR logic 144b for processing. Sometimes small text, when enlarged, achieves greater accuracy in the OCR engine processing.

Color bit: This option may result in the image being reduced to a smaller color set. For example, instead of 24-bits per pixel to represent each pixel's color, the number of different colors could be reduced to 256 (8-bit) or even 2 (1-bit) per pixel.

Image filtering option: There are a wide variety of image filtering and sharpening algorithms available in the field today that could also be employed to further prepare the image for optimal OCR processing.

Once the text fields have been identified and potentially further manipulated, each text field may then be processed via the OCR logic 144b. The relative location of each text field to the full image and ultimately the user's screen may be determined for mapping and/or calculating the coordinates of each character identified. Coordinates may be utilized to perform the action on the screen with the voice command. Depending on the particular embodiment, there may be a variety of configuration options that are appropriate to apply for this particular usage case. For example, such options can include:

Character whitelist: This controls which characters that are allowed to be recognized. Reducing the character set limits the options that the OCR logic 144b may consider when recognizing a character in the image. The end result may be improved accuracy. In these embodiments, a character whitelist of the following characters may be used. This set may be altered for languages that use different character sets.

Digits: 012345679
Symbols: .,""''( )[ ]><\:;-*/
Lower Case Letters: abcdefghijklmnopqrstuvwxyz
Upper Case Letters: ABCDEFGHIJKLMNOPQRSTUVWXYZ Performance Mode: This option controls the number of passes the OCR logic 144b performs on the image. Some OCR engines provide adaptive processing such that improved accuracy can be obtained by processing the image more than once. This may be most effective for small fonts (e.g., less than 10 pt. in size).

Once the output of the OCR logic 144b is provided, additional processing can be helpful to further filter out the results to adjust the text on which a user might want to perform voice commands. These settings include:

Filter Text: This option may be utilized to control whether to filter out apparent erroneous/random text recognized by the OCR logic 144b. Erroneous text can result if image areas that do not really contain text are passed to OCR logic 144b. For example, the target application may have a toolbar with white outlines, but the toolbar does not really contain text applicable for formatting and navigation voice commands. Thus the OCR logic 144b may interpret non-text as characters. This setting helps filter this erroneously identified text out of consideration. For example, if the OCR logic 144b returns a text string of "\[ ]('''', . . . B A 1 1 1 F" as a line of recognized text then the recognized "text" is likely not text that a user will use in a voice command. Also, it is likely that the OCR logic 144b interpreted the erroneous text from a non-text field. Using a variety of character string matching methods most of these erroneous text strings are filtered out.

Check for Left Alignment of Text: This option may attempt to determine a location of the text on the screen that a user may want to interact with voice commands. If the OCR logic 144b returns text from a variety of locations in the image, these embodiments may determine where the largest and most consistent text fields that share the same left alignment are. Once this left alignment is identified, other identified text with a different left alignment outside a variance threshold may be filtered out.

Post word replacement processing: If words are not properly recognized during text recognition, speech commands will likely not perform properly for those words. For example, if the phrase "the patient reported chest pain" is located in a text field on the screen but the OCR logic 144b recognized "the patiant repolted chest pain," and the user spoke the command "SELECT patient reported" the speech application would not be able to find this text for executing the command. Since the text recognition results may be hidden from the user, the user may not know that the text recognition process did not recognize these words properly and the result would just be an unsuccessful voice command. In order to reduce the likelihood of an unsuccessful voice command, it is important to have high accuracy. The algorithms, options, and training data provided within the OCR logic 144b alone may not deliver high enough accuracy, so post processing techniques may be utilized.

One technique to improve accuracy may include using a large document data set (e.g., 100,000 plus documents, 1 million+ words) specific to the context of the user's data (e.g., medical reports) to build a core lookup dictionary of the most frequency used words as well as their bigram and trigram frequency. Bigram frequency refers to how often two particular words appear next to each other (e.g., the patient). Trigram frequency meaning how often three particular words appear next to each other. Low frequency words can be removed as they are unlikely to be found in the target application text fields. After collecting this data, a developed utility can be used to process each word, each frequent bigram and each frequent trigram combinations of words through the OCR logic 144b. Multiple passes may be performed for each common font and point size that is most typically used by target applications. As the text is processed, embodiments may be configured to build a list of the misrecognitions to create word error list. For example, if the OCR logic 144b outputs "repolted" for "reported" these embodiments may save that error into a replacement dictionary. If the OCR logic 144b outputs "patent" for "patient", and the error word "patent" is also a real word then the replacement can still be added if the error word has a much lower usage frequency than the actual word in the lookup dictionary.

Both the core lookup dictionary and the replacement dictionary can then be used by the voice recognition logic 144c after receiving the text results from the OCR logic 144b. For each word returned by the OCR logic 144b, the voice recognition logic 144c can look that word up in the replacement dictionary, and if so replace it with its replacement word. Additionally, the embodiment may further remove characters or replace commonly misrecognized characters with predicted correct characters and search the core lookup dictionary until a match on a valid word is found.

Another common error when text recognizing the image by the OCR logic 144b is to not properly identify spacing between two words. For example, "of the" may be recognized as "of the". To address this issue, each identified word can also be looked up in the core lookup dictionary. If the core lookup dictionary does not have the word, the recognized word can be split in each possible character location and a lookup be performed to see if each portion is a valid word. If so, then the combined word can be replaced with the two individual words.

Additionally, embodiments of the voice recognition logic 144c may be configured to process audio and interpret that audio as voice commands from a user. For recognizing voice commands such as "SELECT [word(s)]" the voice recognition logic 144c may be provided with both a speech grammar file containing the possible commands and an audio stream or file. The list of "word(s)" is obtain from the output of the OCR logic 144b together with any post error correction processing with in the voice recognition logic 144c previously described. If the voice recognition logic 144c does not use a limited list of all the "word(s)" for the SELECT command then the voice recognition logic 144c would allow for a much wider set of possibilities, such as the entire English dictionary, which could result in lower accuracy of recognition results. If the list of words was not limited then the recognition engine could recognize "SELECT word" where the "word" is not contained within the text area. Thus, embodiments of the voice recognition logic 144c may be provided a speech grammar limited to just the available words that the user may want to interact. As described above, both the captured image of recognized text and the known text may be used to build the speech grammar.

The output of the voice recognition logic 144c is the recognized voice command. The voice recognition logic 144c must then process those results and execute the command appropriately. The formatting and navigation speech commands that this system applies to include an action and one or more words that the action is to be applied. For example, "SELECT patient THROUGH visit" has the action components as SELECT THROUGH and words "patient" and "visit." Upon receiving the recognized voice command, the voice recognition logic 144c may determine if the words that the action applies are from the image recognized text or the application known text. The source of the words determines how the execution process for performing the action takes places. Embodiments can include an option such that if the words recognized are in both the application known text and in the image recognized text that the action would be performed on one verses the other. However, since the command execution process for image recognized text is faster than that of application known text, this is likely the preferred option.

Figure 3:
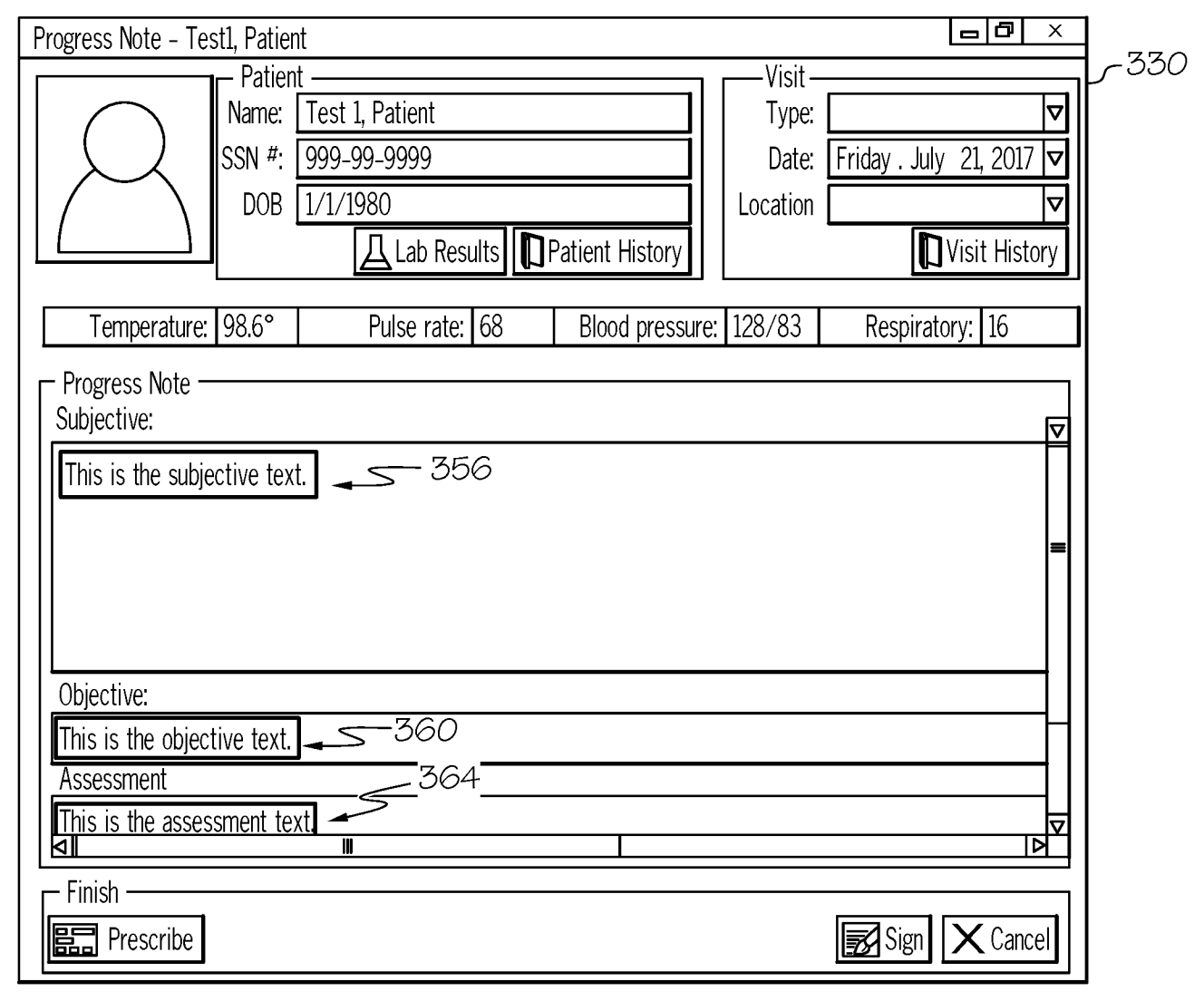

FIG. 3 depicts a user interface 330 indicating text fields for providing voice text formatting and navigation commands, according to embodiments described herein. As illustrated, the user computing device 102 has captured an image of the user interface 330. The user computing device 102 has also identified the text fields from the image and performed a text recognition process on the identified text fields. As illustrated in box 356, 360, and 364, using the techniques for Only Process Target Color Text Fields and Trim Text Fields previously described, only identified text areas are used as input into OCR logic 144b. Additionally, a user may provide a voice command, such as "DELETE 'has been'." In response, embodiments may automatically select that phrase by identifying the first coordinates required to place the cursor by simulating a mouse click; determine the second coordinates on the opposite side of the phrase; select the phrase by simulating a mouse click; and delete the selected phrase.

Figure 4:
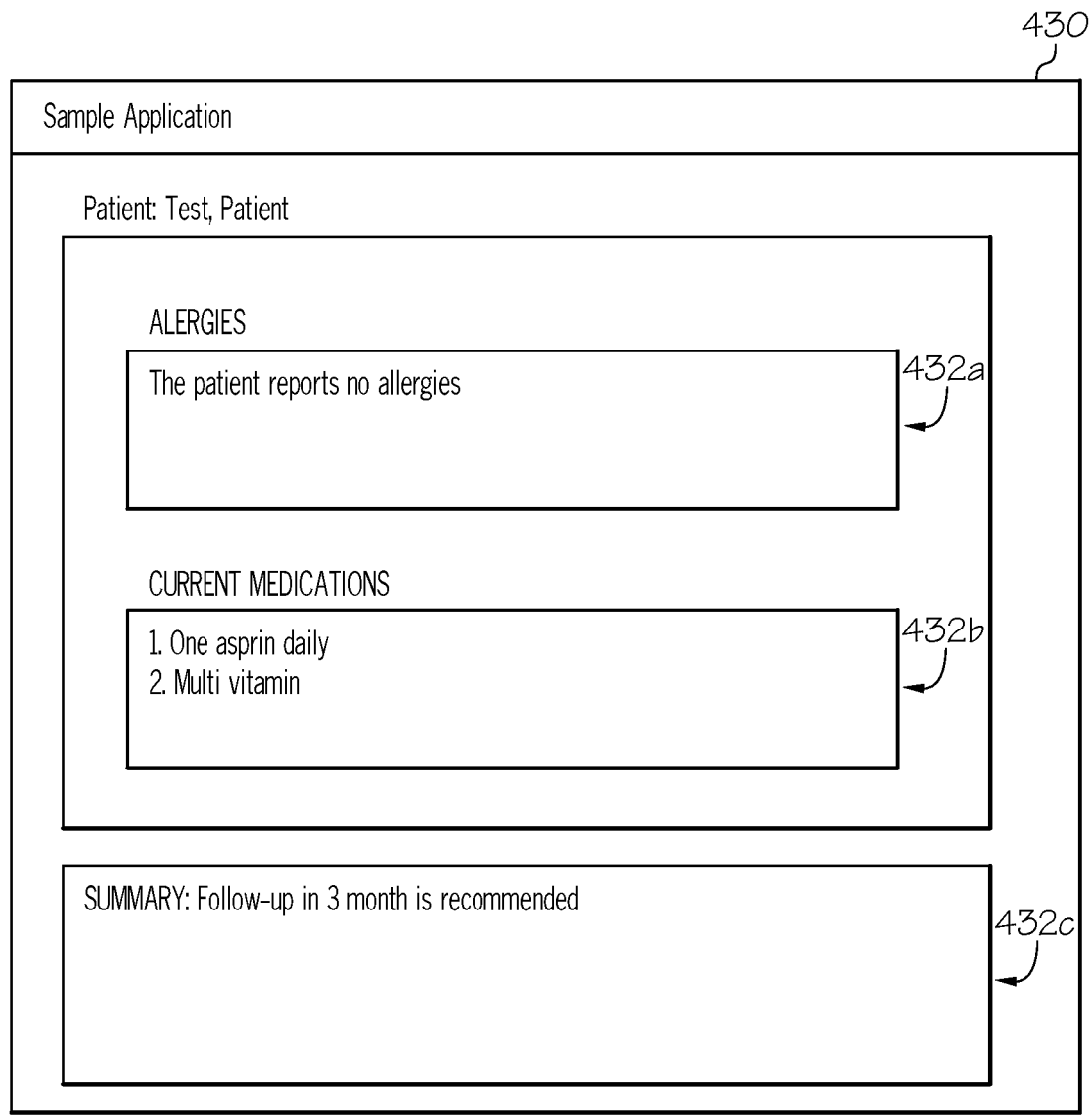
FIG. 4 depicts another user interface including text fields for providing voice text formatting and navigation commands, according to embodiments described herein.

FIG. 4 depicts another user interface 430 including text fields for providing voice text formatting and navigation commands, according to embodiments described herein. As discussed above, different target applications (and different interfaces provided by the same target application) may provide different formats of text fields. Specifically, while the user interfaces of FIGS. 2 and 3 include text fields that are distinguishable from the non-text fields, FIG. 4 only includes a single line between text fields 432a, 432b, 432c and non-text fields. As such, embodiments may be configured to alter the process for determining the text fields, depending on the application.

Figure 5:
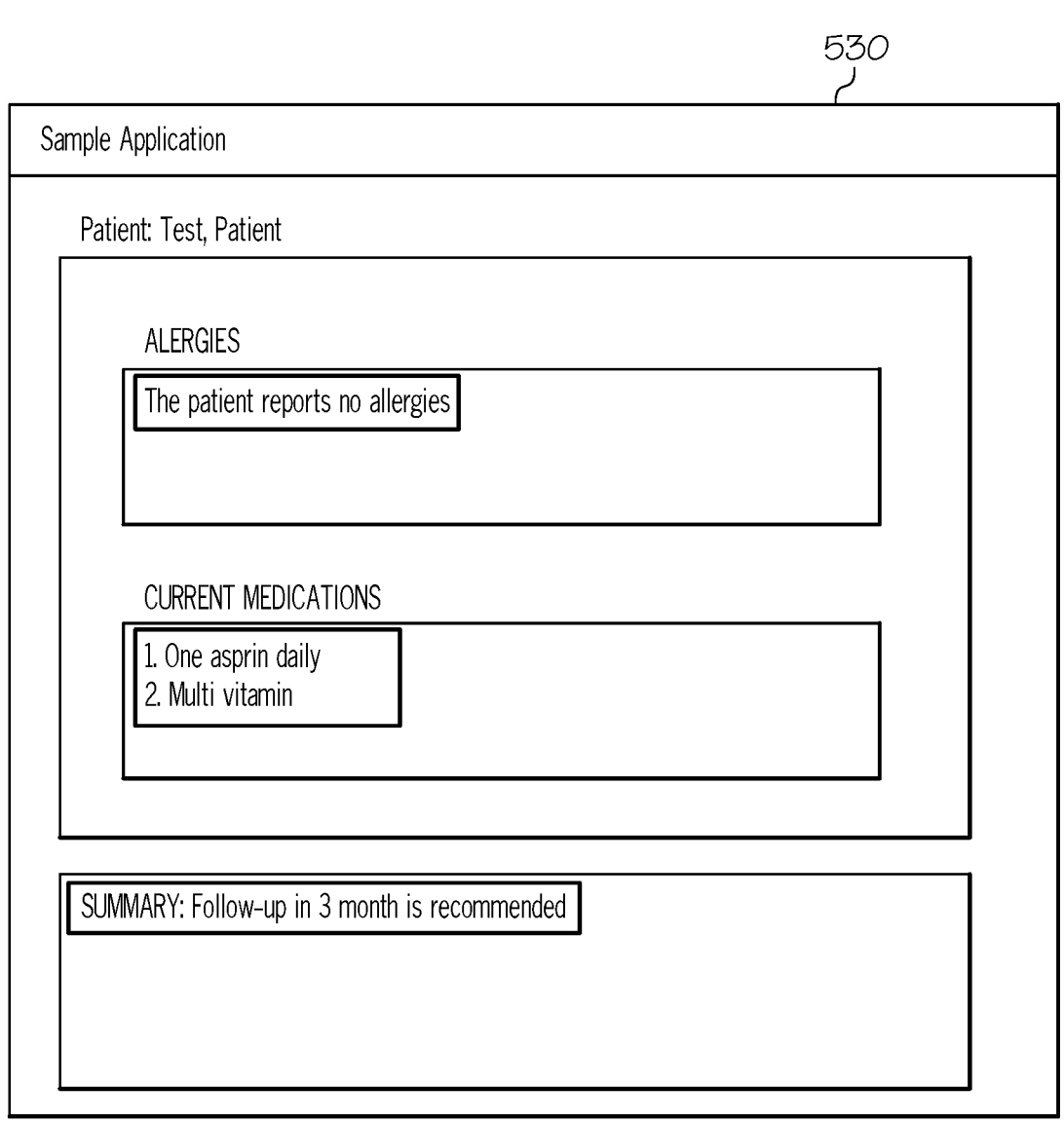
FIG. 5 depicts another user interface indicating text fields for providing voice text formatting and navigation commands, according to embodiments described herein.

FIG. 5 depicts another user interface 530 indicating text fields for providing voice text formatting and navigation commands, according to embodiments described herein. Similar to the user interface 330 from FIG. 3, the user computing device 102 has identified the text fields with boxes around the text illustrating the text areas processed by the OCR logic 144b. While in some embodiments, these boxes are provided to the user for easily identifying which fields may be subject to voice commands.

Figure 6:
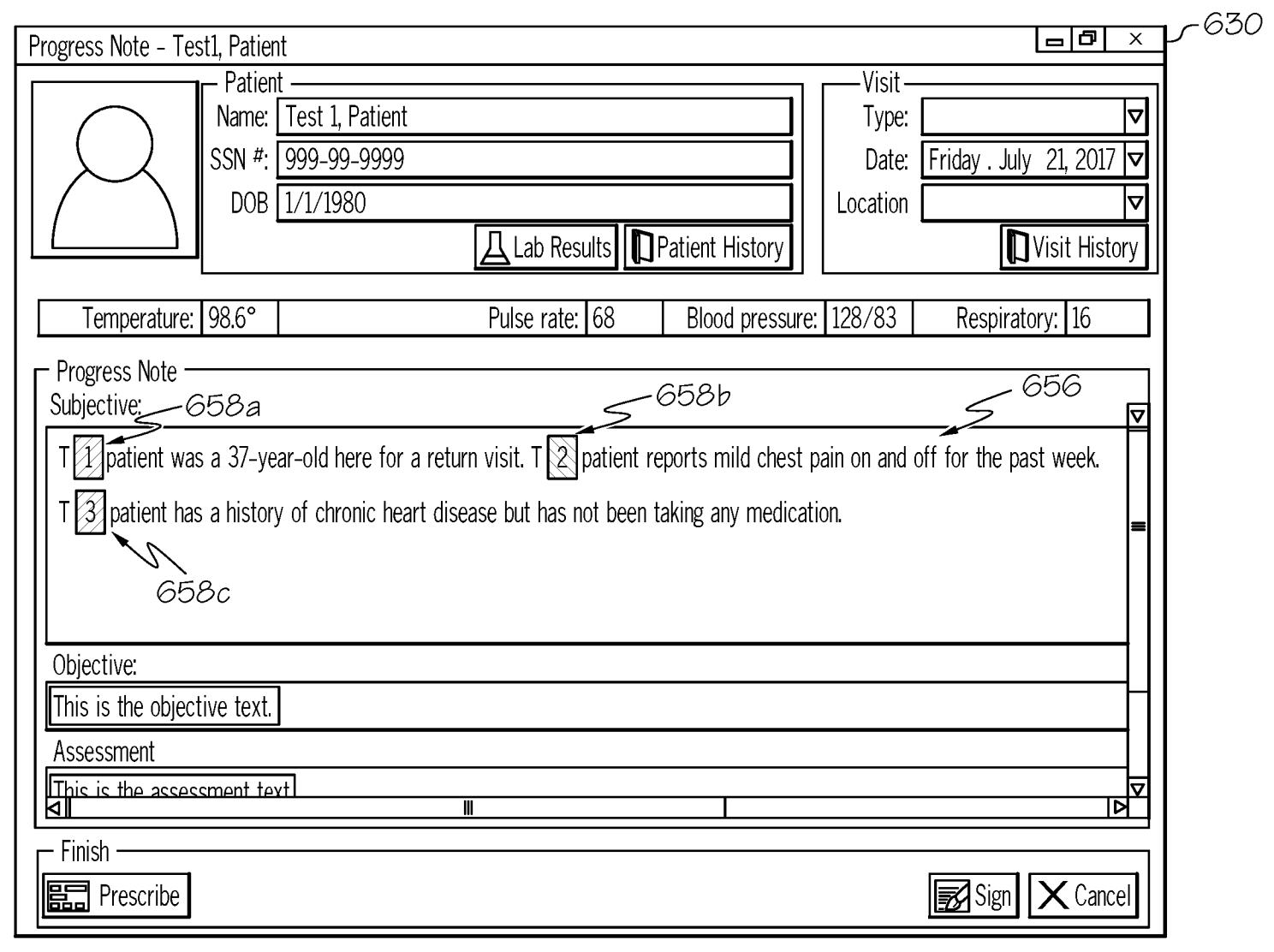

FIG. 6 depicts a user interface 630 that identifies options when a voice command applies to a plurality of sections of a text field, according to embodiments described herein. As illustrated, the user computing device 102 has captured an image of the user interface 630 and has performed text recognition of the text field 656. In this example, however, there is at least one word ("patient") that was repeated in the text field 656. If the user provides a voice command that includes this repeated word, the user computing device 102 may have to distinguish which "patient" the user is referring.

As such, some embodiments may be configured to provide identifiers 658a, 658b, 658c that distinguish each instance of a plurality of instances of the repeated word such that the user may include the identifier in the voice command. As an example, the user may provide a command such as "DELETE "the first 'patient'" or "DELETE 'patient 1.'" This provides the user computing device 102 with the appropriate information for executing the voice command.

It should be understood that some embodiments may be configured to provide the identifiers 658a, 658b, 658c in response to a receiving a user command with the repeated word. However, some embodiments may be configured to provide one or more of the identifiers 658a, 658b, 658c upon performing the text recognition and/or at other times.

It should also be understood that while a user may desire to execute the voice command on a single instance of the repeated word, this is one example. In some embodiments, the user may provide an additional command word (such as "GLOBAL") to indicate that the command should be executed on all instances. Similarly, some embodiments may be configured for the user to indicate that more than one of the instances are applicable, such as by selecting those identifiers that apply (such as 658a, 658b). In some embodiments, the input devices 108a, 108b on the microphone 106 from FIG. 1 (and/or other user options) may be utilized to scroll or select specific instances of the repeated word.

Figure 7:
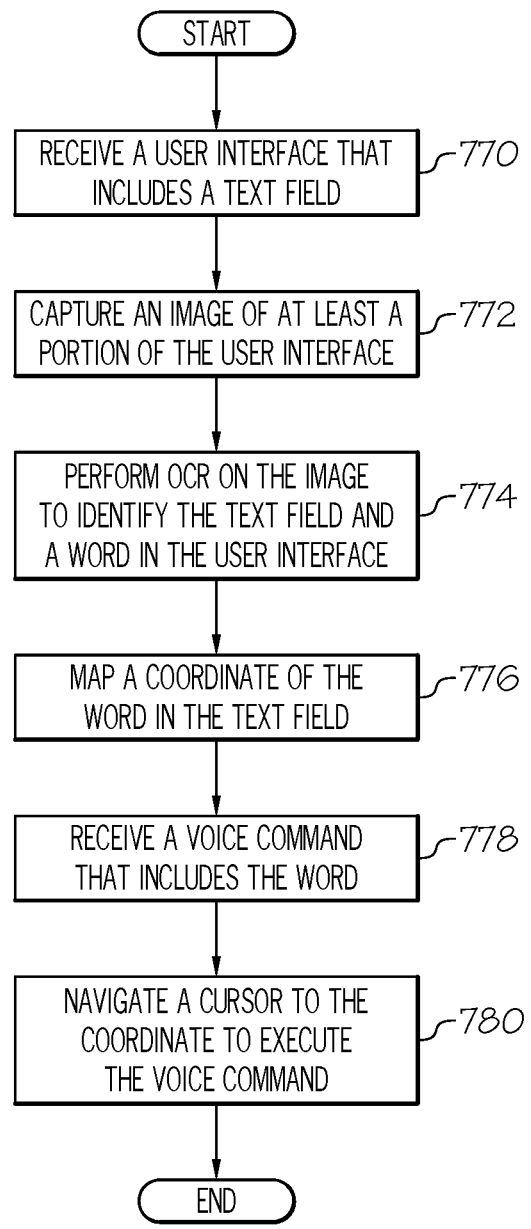
FIG. 7 depicts a flowchart for executing a voice command, according to embodiments described herein.

FIG. 7 depicts a flowchart for executing a voice command, according to embodiments described herein. As illustrated in block 770, a user interface that includes a text field may be received. In block 772, an image of at least a portion of the user interface may be captured. In block 774, OCR may be performed on the image to identify the text field and a word in the user interface. In block 776, a coordinate of the word in the text field may be mapped. In block 778, a voice command that includes the word may be received. In block 780, a cursor may be navigated to the coordinate to execute the voice command.

Figure 8:
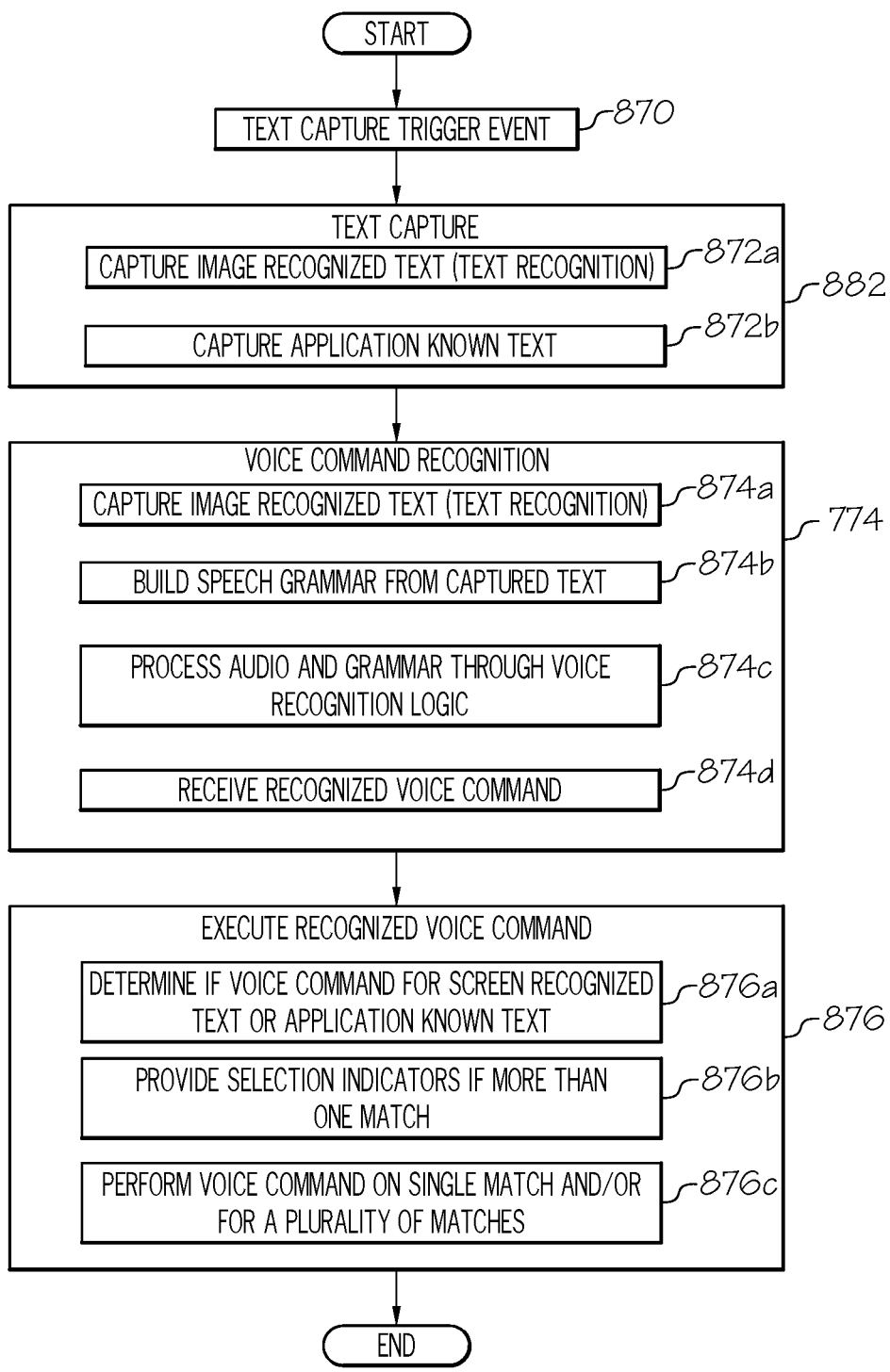
FIG. 8 depicts a flowchart for receiving a voice command with an OCR capability and a plurality of voice command matches, according to embodiments described herein.

FIG. 8 depicts a flowchart for receiving a voice command with an OCR capability and a plurality of voice command matches, according to embodiments described herein. As illustrated in block 870, a text capture trigger event may be received and/or detected. Specifically, the text capture trigger event include, but not be limited to, opening a target application, user picking up a hand held microphone, receiving a voice command, receiving recognized text, clicking the mouse, pressing a key, etc. In block 872, text capture may be performed, which might include capturing image of recognized text in block 872a and/or capturing application known text in block 872b. As described above, an image of a user interface may be captured and a text recognition process may then be performed to identify editable text. Additionally, some text provided in the user interface may already be identified as editable due to the user inputting the text in to the target application.

In block 874, voice command recognition may be performed. Specifically, in block 874a, audio may be captured from the microphone 106. In block 874b, a speech grammar may be built from the captured text. In block 874c, audio and the grammar may be processed via the voice recognition logic 144c. In block 874d, the recognized voice command may be received.

In block 876, the recognized voice command may be executed. In block 876a, a determination may be made whether the voice command is associated with screen recognized text and/or application known text. In block 876b, selection indicators may be provided if more than one match for the voice command. In block 876c voice command may be performed on a single match and/or for a plurality of matches.

Figure 9:
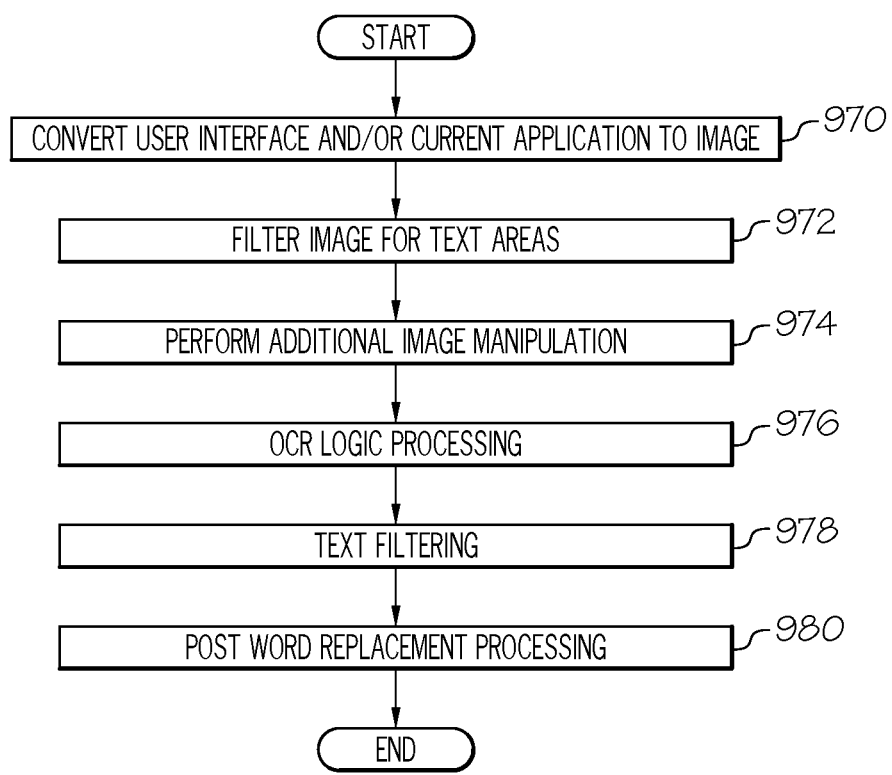
FIG. 9 depicts a flowchart for processing text for utilizing a voice command, according to embodiments described herein.

FIG. 9 depicts a flowchart for processing text for utilizing a voice command, according to embodiments described herein. As illustrated in block 970, a user interface and/or target application may be converted to an image. In block 972, the image may be filtered for text fields. In block 974, additional image manipulation may be performed (as described above). In block 976, the OCR logic 144b may process the image to identify text therein. In block 978, the text may be filtered. In block 980, post word replacement processing may be performed.

Figure 10:
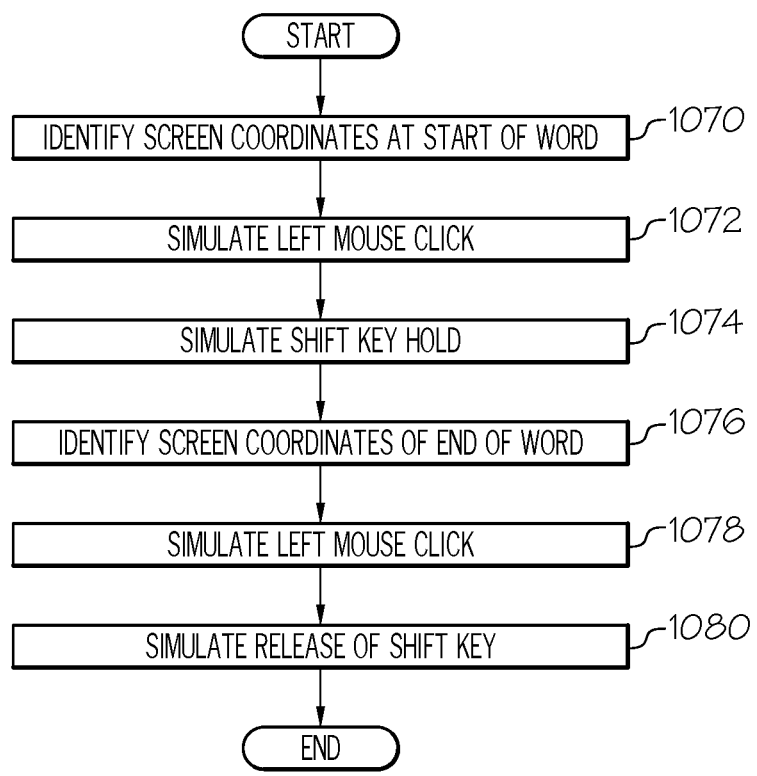
FIG. 10 depicts a flowchart for simulating application commands with voice commands, according to embodiments described herein.

FIG. 10 depicts a flowchart for simulating application commands with voice commands, according to embodiments described herein. Specifically, once the user interface has been analyzed and the voice command has been received, the voice command may be executed. As illustrated in block 1070, screen coordinates may be identified and/or mapped at a start of a word that is subject to the voice command. In block 1072, a left mouse click may be simulated. In block 1074, a shift key hold may be simulated. In block 1076 screen coordinates for the end of the word may be identified and/or mapped. In block 1078, a left mouse click may again be simulated. In block 1080, a release of the shift key may be simulated. This sequence of actions selects the desired word, which may be acted upon according to the received voice command.

Figure 11:
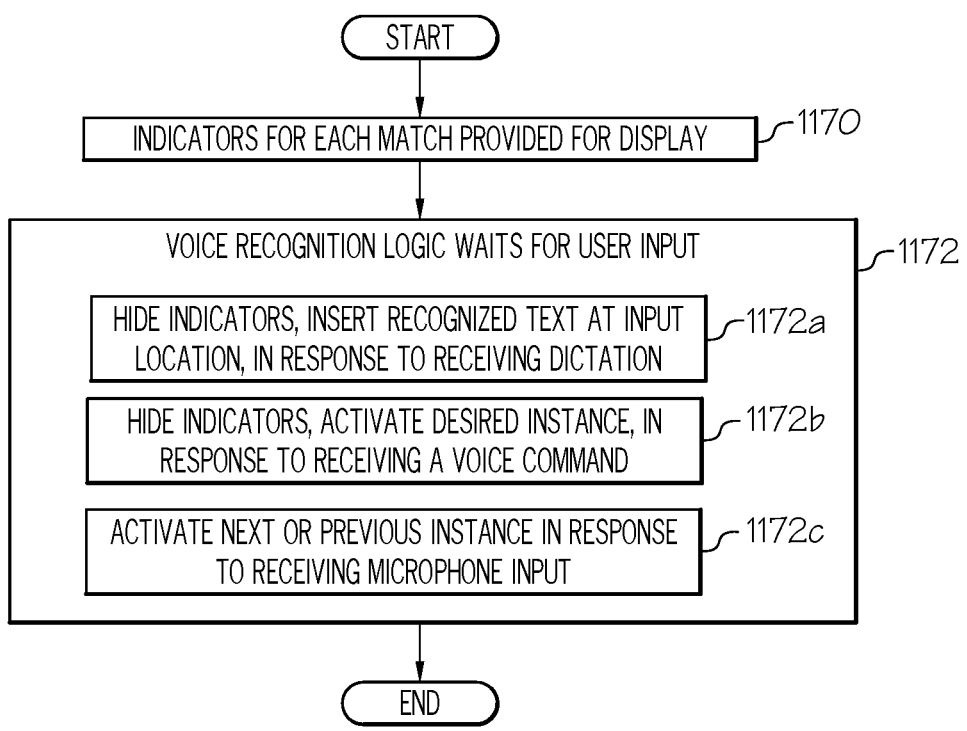
FIG. 11 depicts a flowchart for simulating application commands with a plurality of different commands, according to embodiments described herein.

FIG. 11 depicts a flowchart for simulating application commands with a plurality of different commands, according to embodiments described herein. As illustrated in block 1170, indicators for each word match may be provided for display. In block 1172, the voice recognition logic 144c waits for user input that includes a voice command. In block 1172a, in response to receiving dictation of additional text, indicators may be hidden and the recognized text may be inserted at the input location (e.g., location of the cursor). In block 1172b, in response to receiving a voice command, the indicators may be hidden and the desired instance of the word may be activated. In block 1172c, in response to receiving microphone input (e.g., via the input devices 108a, 108b from FIG. 1), a next or previous instance of the word may be activated.

Figure 12:
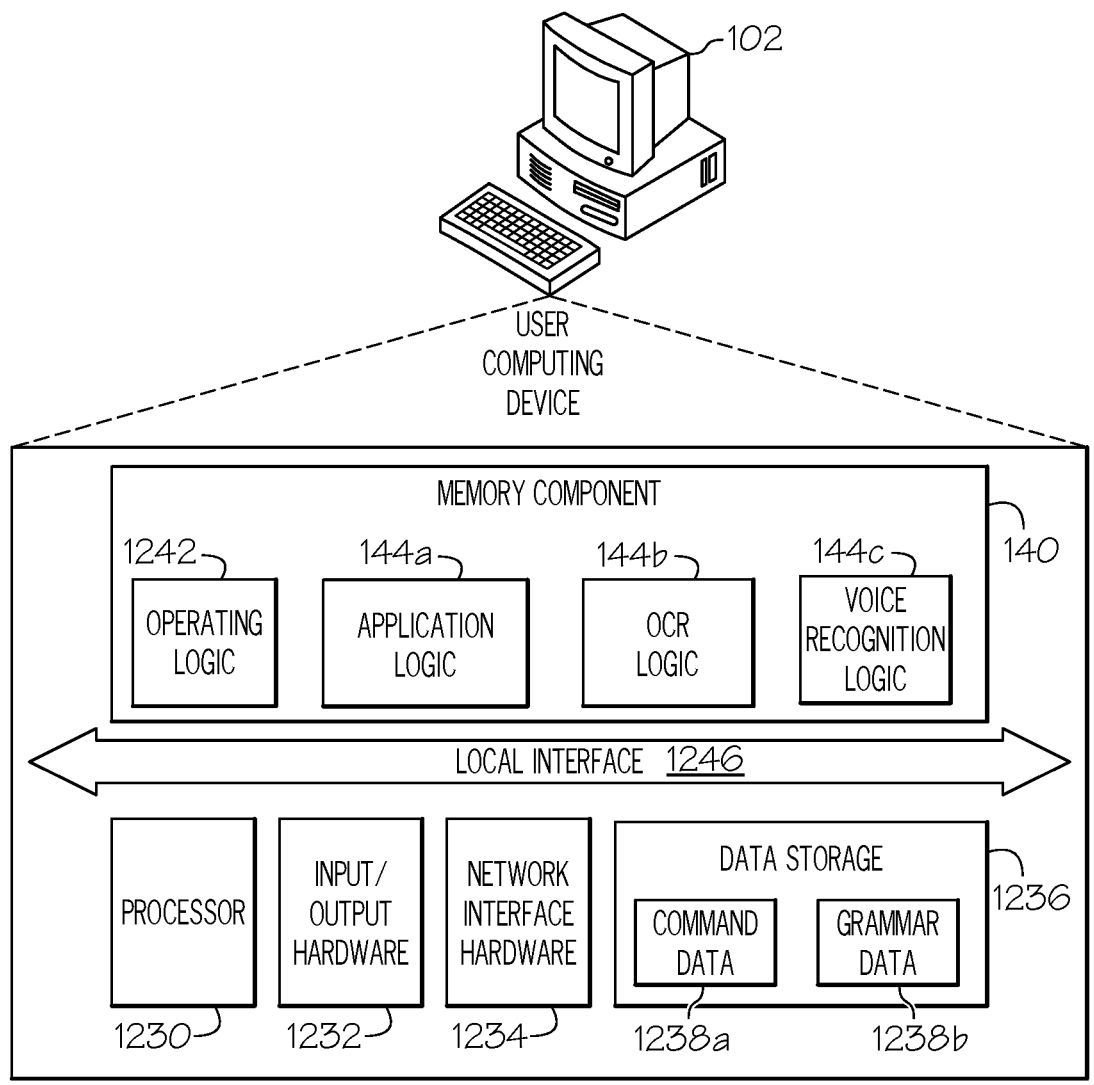
FIG. 12 depicts a user computing device for using optical character recognition with voice recognition commands, according to embodiments described herein.

FIG. 12 depicts a user computing device 102 for using optical character recognition with voice recognition commands, according to embodiments described herein. As illustrated, the user computing device 102 includes a processor 1230, input/output hardware 1232, network interface hardware 1234, a data storage component 1236 (which stores command data 1238a, grammar data 1238b, and/or other data), and the memory component 140. The memory component 140 may be configured as volatile and/or nonvolatile memory and as such, may include random access memory (including SRAM, DRAM, and/or other types of RAM), flash memory, secure digital (SD) memory, registers, compact discs (CD), digital versatile discs (DVD), and/or other types of non-transitory computer-readable mediums. Depending on the particular embodiment, these non-transitory computer-readable mediums may reside within the user computing device 102 and/or external to the user computing device 102.

The memory component 140 may store operating logic 1242, the application logic 144a, the OCR logic 144b, and the voice recognition logic 144c. The application logic 144a, the OCR logic 144b, and the voice recognition logic 144c may each include a plurality of different pieces of logic, each of which may be embodied as a computer program, firmware, and/or hardware, as an example. A local interface 1246 is also included in FIG. 12 and may be implemented as a bus or other communication interface to facilitate communication among the components of the user computing device 102.

The processor 1230 may include any processing component operable to receive and execute instructions (such as from a data storage component 1236 and/or the memory component 140). The input/output hardware 1232 may include and/or be configured to interface with microphones, speakers, a display, and/or other hardware.

The network interface hardware 1234 may include and/or be configured for communicating with any wired or wireless networking hardware, including an antenna, a modem, LAN port, wireless fidelity (Wi-Fi) card, WiMax card, ZigBee card, Bluetooth chip, USB card, mobile communications hardware, and/or other hardware for communicating with other networks and/or devices. From this connection, communication may be facilitated between the user computing device 102 and other computing devices, such as the remote computing device 104.

The operating logic 1242 may include an operating system and/or other software for managing components of the user computing device 102. As also discussed above, the application logic 144a, the OCR logic 144b, and the voice recognition logic 144c may reside in the memory component 140 and may be configured to perform the functionality, as described herein.

It should be understood that while the components in FIG. 12 are illustrated as residing within the user computing device 102, this is merely an example. In some embodiments, one or more of the components may reside external to the user computing device 102. It should also be understood that, while the user computing device 102 is illustrated as a single device, this is also merely an example. In some embodiments, the application logic 144a, the OCR logic 144b, and the voice recognition logic 144c may reside on different computing devices. As an example, one or more of the functionalities and/or components described herein may be provided by a user computing device 102 and/or the remote computing device 104, which may be coupled to the user computing device 102 via the network 100.

Additionally, while the user computing device 102 is illustrated with the application logic 144a, the OCR logic 144b, and the voice recognition logic 144c as separate logical components, this is also an example. In some embodiments, a single piece of logic (and/or or several linked modules) may cause the user computing device 102 to provide the described functionality.

As illustrated above, various embodiments for using optical character recognition with voice recognition commands are disclosed. These embodiments allow the user not to have to use the mouse to navigate to the area and then manually highlight the selection with the mouse. This also applies to touch screen devices where a user may user their finger or stylus instead of a mouse. This is also helpful in a hands free environment where the user must be using their hands for other tasks. If performed quickly enough, a voice command can take a shorter amount of time to recognize and execute then for the user to use a mouse to do the same action.

While particular embodiments and aspects of the present disclosure have been illustrated and described herein, various other changes and modifications can be made without departing from the spirit and scope of the disclosure. Moreover, although various aspects have been described herein, such aspects need not be utilized in combination. Accordingly, it is therefore intended that the appended claims cover all such changes and modifications that are within the scope of the embodiments shown and described herein.

It should now be understood that embodiments disclosed herein include systems, methods, and non-transitory computer-readable mediums for using optical character recognition with voice recognition commands. It should also be understood that these embodiments are merely exemplary and are not intended to limit the scope of this disclosure.

What is claimed is:

1. A method for using optical character recognition (OCR) with voice recognition commands comprising:
  receiving, by a computing device, a user interface that includes a text field for receiving text that is input by a user;
  capturing, by the computing device, an image of at least the text field in the user interface;
  performing, by the computing device, OCR on the image;
  identifying, by the computing device, the text field from the image and a word in the text from the OCR, wherein identifying the text field includes identifying a characteristic of the text field that defines an area into which a user provides textual input;
  mapping, by the computing device, a coordinate of the word in the text field;
  receiving, by the computing device, a voice command to perform an action on or around the word in the text field;
  navigating, by the computing device, a cursor to the coordinate; and
  executing, by the computing device, the command on or around the word in the text field.

2. The method of claim 1, wherein the user interface includes a plurality of instances of the word and wherein, in response to receiving the voice command, indicators are provided on at least two of the plurality of instances of the word to determine to which of the instances the voice command applies.

3. The method of claim 1, further comprising performing post word replacement processing on the word to improve accuracy of the OCR.

4. The method of claim 1, further comprising performing image manipulation, wherein image manipulation includes at least one of the following: altering a scale factor, altering color bit depth, or filtering the image.

5. The method of claim 1, wherein identifying the characteristic that defines the area into which the user enters text includes performing at least one of the following: identifying a target color text field, identifying a maximum threshold RGB value, identifying a minimum threshold RGB value, identifying a minimum text field height, identifying a minimum text field width, trimming the text field, or identifying a minimum text field border.

6. The method of claim 1, wherein performing OCR includes utilizing a character whitelist.

7. The method of claim 1, wherein identifying the text field includes performing at least one of the following: filtering erroneously recognized text or determining a left alignment of text found in the OCR.

8. A system for using optical character recognition (OCR) with voice recognition commands comprising:
  a computing device that includes a memory component and a processor, the memory component storing application logic, OCR logic, and voice recognition logic that, when executed by the processor, causes the computing device to perform at least the following:
  receive, via the application logic, a user interface that includes an editable text field, wherein the application logic provides a target application;
  capture, via the voice recognition logic, an image of at least the editable text field in the user interface;
  perform, via the OCR logic, OCR on the image to identify the editable text field and a word in the editable text field of the user interface;
  map, via the voice recognition logic, a coordinate of the word in the editable text field;
  receive, via the voice recognition logic, a voice command to perform an action on or around the word;
  navigate, via the voice recognition logic, a cursor to the coordinate; and
  execute, via the voice recognition logic, the voice command to perform the action on or around the word in the target application.

9. The system of claim 8, wherein the user interface includes a plurality of instances of the word and wherein, in response to receiving the voice command, indicators are provided on at least two of the plurality of instances of the word to determine to which of the instances the voice command applies.

10. The system of claim 8, wherein the OCR logic further causes the computing device to perform post word replacement processing on the word to improve accuracy of the OCR.

11. The system of claim 8, wherein the OCR logic further causes the computing device to perform image manipulation, wherein the image manipulation includes at least one of the following: altering a scale factor, altering color bit depth, or filtering the image.

12. The system of claim 8, wherein identifying the editable text field includes performing at least one of the following: identifying a target color text field, identifying a maximum threshold RGB value, identifying a minimum threshold RGB value, identifying a minimum text field height, identifying a minimum text field width, trimming the text field, or identifying a minimum text field border.

13. The system of claim 8, wherein performing OCR includes utilizing a character whitelist.

14. The system of claim 8, wherein identifying the editable text field includes performing at least one of the following: filtering erroneously recognized text or determining a left alignment of text found in the OCR.

15. A non-transitory computer-readable medium for using optical character recognition (OCR) with voice recognition commands that, when executed by a computing device, causes the computing device to perform at least the following: receive a user interface that includes a text field for receiving text that is input by a user;
    capture an image of at least the text field in the user interface;
    perform OCR on the image;
    identify the text field from the image and a word in the text from the OCR, wherein
    identifying the text field includes identifying a characteristic of the text field that defines an area into which a user provides textual input;
    map a coordinate of the word in the text field;
    receive a voice command to perform an action on or around the word;
    navigate a cursor to the coordinate; and
    execute the voice command to perform the action on or around the word in a target application.

16. The non-transitory computer-readable medium of claim 15, wherein the user interface includes a plurality of instances of the word and wherein, in response to receiving the voice command, indicators are provided on at least two of the plurality of instances of the word to determine to which of the instances the voice command applies.

17. The non-transitory computer-readable medium of claim 15, wherein the logic further causes the computing device to perform post word replacement processing on the word to improve accuracy of the OCR.

18. The non-transitory computer-readable medium of claim 15, wherein the logic further causes the computing device to perform image manipulation, wherein the image manipulation includes at least one of the following: altering a scale factor, altering a color bit, or filtering the image.

19. The non-transitory computer-readable medium of claim 15, wherein identifying the characteristic of the text field that defines the area into which a user enters text includes performing at least one of the following: identifying a target color text field, identifying a maximum threshold RGB value, identifying a minimum threshold RGB value, identifying a minimum text field height, identifying a minimum text field width, trimming the text field, or identifying a minimum text field border.

20. The non-transitory computer-readable medium of claim 15, wherein performing OCR includes utilizing a character whitelist.

* * * * *